US009629874B2

(12) United States Patent
Tsirikos-Karapanos (10) Patent No.: US 9,629,874 B2
(45) Date of Patent: Apr. 25, 2017

(54) PRODUCTION OF WATER-SOLUBLE HYDROLYZED CLINOPTILOLITE FRAGMENTS AND NUTRACEUTICAL PRODUCTS BASED ON WATER-SOLUBLE HYDROLYZED CLINOPTILOLITE FRAGMENTS

(71) Applicant: Nikolaos Tsirikos-Karapanos, Cleveland, OH (US)

(72) Inventor: Nikolaos Tsirikos-Karapanos, Cleveland, OH (US)

( * ) Notice: Subject to any disclaimer, the term of this patent is extended or adjusted under 35 U.S.C. 154(b) by 0 days.

(21) Appl. No.: 14/879,233

(22) Filed: Oct. 9, 2015

(65) Prior Publication Data

US 2016/0367595 A1 Dec. 22, 2016

Related U.S. Application Data

(63) Continuation of application No. PCT/US2014/072923, filed on Dec. 31, 2014.

(60) Provisional application No. 62/061,898, filed on Oct. 9, 2014.

(51) Int. Cl.
| | |
|---|---|
| *A61K 33/06* | (2006.01) |
| *A61K 9/00* | (2006.01) |
| *A61K 31/198* | (2006.01) |
| *A61K 31/375* | (2006.01) |
| *A61K 31/405* | (2006.01) |
| *A61K 36/185* | (2006.01) |
| *A61K 36/28* | (2006.01) |
| *A61K 36/35* | (2006.01) |
| *A61K 36/752* | (2006.01) |
| *C01B 39/46* | (2006.01) |
| *A23L 5/20* | (2016.01) |
| *A23L 33/16* | (2016.01) |
| *A23L 33/15* | (2016.01) |

(52) U.S. Cl.
CPC .............. *A61K 33/06* (2013.01); *A23L 5/276* (2016.08); *A23L 33/15* (2016.08); *A23L 33/16* (2016.08); *A61K 9/0053* (2013.01); *A61K 31/198* (2013.01); *A61K 31/375* (2013.01); *A61K 31/405* (2013.01); *A61K 36/185* (2013.01); *A61K 36/28* (2013.01); *A61K 36/35* (2013.01); *A61K 36/752* (2013.01); *C01B 39/46* (2013.01); *A23V 2002/00* (2013.01)

(58) Field of Classification Search
CPC ....... A23L 33/15; A23L 33/16; A61K 31/375; A61K 33/06; C01B 39/46
See application file for complete search history.

(56) References Cited

U.S. PATENT DOCUMENTS

| | | |
|---|---|---|
| 6,288,045 B1 | 9/2001 | Kaufman |
| 2002/0034543 A1 | 3/2002 | Kirschner et al. |

FOREIGN PATENT DOCUMENTS

| | | |
|---|---|---|
| WO | 00/75079 A1 | 12/2000 |
| WO | 2008092275 A1 | 8/2008 |

OTHER PUBLICATIONS

SaltsClaysMinerals.com (http://www.saltsclaysminerals.com/natural/ZC-20.html, Natural Zeolite Clinoptilolite <40 Micron, 2016).*
Pansini (Mineral Deposita, 1996, vol. 31, pp. 563-575).*
Akkoca et al (Geochemistry International, Jun. 2013, vol. 54, pp. 495-504).*
Hernandez-Beltran et al (J Incl Phenom Macrocycl Chem, 2008, vol. 61, pp. 93-100).*
Akkoca et al., "Hydrothermal and thermal treatment of natural clinoptilolite zeolite from Bigadi double dagger, Turkey: An experimental study", Geochemistry International, Jun. 2013, vol. 54(6).
De las Pozas et al., "Modification of clinoptilolite by leaching with orthophosphoric acid", Microporous Materials, Jan. 1996, vol. 5(5).
Kaufman, Harvey, "Modern Detox for Today's Toxic World (ZNatural)", Dec. 31, 2013.
Hernandez-Beltran et al., "Effect of acid phosphate media on the stability of clinoptilolite-rich tuff", Jun. 30, 2008.
Karel et al., "Development of Silver Ion Doped Antibacterial Clays and Investigation of Their Antibacterial Activity", Dec. 31, 2015.
Panneerselvam et al., "Phosphoric acid modified-Y zeolites: A novel, efficient and versatile ion exchanger", Nov. 11, 2008.
Murphy et al., "Reaction kinetics and thermodynamics of aqueous dissolution and growth of analcime and Na-clinoptilolite at 25 degrees C", Feb. 29, 1996.
Liberti et al., "Phosphates and Ammonia Recovery From Secondary Effluents by Selective Ion-Exchange With Production of a Slow-Release Fertilizer", Jan. 31, 1979.
Ku et al., "Dealumination of clinoptilolite and its effect on zinc removal from acid rock drainage", Sep. 30, 2014.

* cited by examiner

*Primary Examiner* — Mark V Stevens
(74) *Attorney, Agent, or Firm* — Ward Law Office LLC; Jacob M. Ward (57) ABSTRACT

Methods are provided to make clinoptilolite into a water-soluble hydrolyzed form suitable for various administration routes, including oral administration. Absorption of water-soluble hydrolyzed clinoptilolite fragments can aid in detoxification by binding heavy metals and environmental toxins, can reducing reactive oxygen species and inflammation related to heavy metals, resulting in an increase in energy, an increase in one or more of focus, concentration, and memory. Water-soluble hydrolyzed clinoptilolite fragments can be combined with one or more dietary supplements, including various vitamins and sleep aids.

16 Claims, 9 Drawing Sheets

PRODUCTION OF WATER-SOLUBLE HYDROLYZED CLINOPTILOLITE FRAGMENTS AND NUTRACEUTICAL PRODUCTS BASED ON WATER-SOLUBLE HYDROLYZED CLINOPTILOLITE FRAGMENTS

CROSS-REFERENCE TO RELATED APPLICATIONS

This application claims the benefit of U.S. Provisional Application No. 62/061,898, filed on Oct. 9, 2014, and International Application No. PCT/US2014/072923, filed on Dec. 31, 2014. The entire disclosures of the above applications are incorporated herein by reference.

FIELD

The present technology relates to ways of making and using water-soluble and bio-absorbable clinoptilolite fragments and compositions thereof.

BACKGROUND

This section provides background information related to the present disclosure which is not necessarily prior art.

The zeolite clinoptilolite, a microporous arrangement of silica and alumina tetrahedra (e.g., sodium aluminosilicate) is a non-water-soluble, non-bioabsorbable salt with a three dimensional honeycomb configuration. Due to its three dimensional configuration, clinoptilolite can attract and retain various heavy metals in vitro. Based on this property, clinoptilolite is used in commercially available filters in various applications ranging from household water filtration to oil industry gas filtration. Several attempts have been made to take advantage of the properties of clinoptilolite in vivo. Such attempts, including associated commercially available nutrition supplement products, have included simple water suspensions of clinoptilolite and not water-soluble solutions thereof. These products fail to bring clinoptilolite's ability to remove heavy metals in vivo. If orally administered, a clinoptilolite water suspension will release clinoptilolite into the gastrointestinal (GI) tract, but this will not result in GI absorption of clinoptilolite. Clinoptilolite administered in this fashion is simply eliminated from the body after a number of bowel movements.

There is a need for a water-soluble clinoptilolite formulation that can be orally administered and absorbed in the GI tract, where the absorbed clinoptilolite retains the ability to bind various heavy metals.

SUMMARY

In concordance with the instant disclosure, a water-soluble clinoptilolite formulation that can be orally administered and absorbed in the GI tract, where the absorbed clinoptilolite retains the ability to bind various heavy metals, is surprisingly discovered.

The present technology includes compositions and methods that relate to formation and use of a water-soluble and bio-absorbable hydrolyzed clinoptilolite derived product, which can be used as a supplement within the scope of cellular detoxification. Water-soluble hydrolyzed clinoptilolite fragments can be absorbed in the GI tract and can be used alone or in combination with various components as a dietary supplement. Compositions include water-soluble hydrolyzed clinoptilolite fragments and a dietary supplement, such as a vitamin, mineral, fiber, fatty acid, amino acid, herb, herbal extract, and combinations thereof. In certain embodiments, water-soluble hydrolyzed clinoptilolite fragments are combined with vitamin C. In some embodiments, water-soluble hydrolyzed clinoptilolite fragments are combined with a sleep aid, such as L-tryptophan, L-theanine, chamomile, lemon balm, passion flower, hops, valerian, and combinations thereof.

Methods of making water-soluble hydrolyzed clinoptilolite fragments are provided. Such methods include performing a hydrolysis reaction by hydrolyzing clinoptilolite with an acid and separating the hydrolysis reaction into a liquid portion and a solid portion, the liquid portion including a hydrolysis reaction product including water-soluble hydrolyzed clinoptilolite fragments. Phosphoric acid can be used in the hydrolysis reaction. The hydrolysis reaction can also involve heating and agitating the clinoptilolite and acid.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology includes water-soluble hydrolyzed clinoptilolite fragments, compositions including water-soluble hydrolyzed clinoptilolite fragments, and methods of making water-soluble hydrolyzed clinoptilolite fragments. Clinoptilolite can include a natural zeolite with a microporous arrangement of silica and alumina tetrahedra. Clinoptilolite has the IUPAC name aluminum sodium dioxido (oxo) silane, and can be referred to as sodium aluminosilicate or aluminum sodium silicate. Its structure can include an outer framework of silica and alumina tetrahedra, within which water molecules and exchangeable cations (e.g., calcium, potassium, sodium) can migrate. The molecular formula of clinoptilolite can vary in composition, where representative examples can be embodied by the following molecular formulas: $(K_{0.1}Na_{0-1}Ca_{0-0.5})_6(Al_6Si_{30}O_{72})\square 2H_2O$; $(Na,K,Ca)_{2-3}Al_3(Al,Si)_2Si_{13}O_{36} \cdot 12H_2O$; $(Na_2,K_2,Ca)_3Al_6Si_{30}O_{72} \cdot 24H_2O$; and $(Na,K)_6(Al_6Si_{30}O_{72})\square 20H_2O$. As provided herein, water-soluble hydrolyzed clinoptilolite fragments include aqueous solutions of water-soluble and bio-absorbable mixtures of zeolite clinoptilolite fragments. Water-soluble hydrolyzed clinoptilolite fragments can be produced by hydrolyzing natural zeolite clinoptilolite under heating with the use of an acid, such as phosphoric acid.

A natural zeolite including clinoptilolite can be hydrolyzed to form water-soluble hydrolyzed clinoptilolite fragments. The natural zeolite can be made water-soluble and provide a certain profile of hydrolyzed fragments using the processes disclosed herein. Examples of natural zeolites include zeolites from St. Cloud Mining Company (Winston, N. Mex.), including clinoptilolite obtained from Winston, N. Mex. that includes calcium aluminosilicate and clinoptilolite obtained from Ash Meadows, Nev. that includes sodium aluminosilicate.

In certain embodiments, the natural zeolite that is hydrolyzed to form water-soluble hydrolyzed clinoptilolite fragments is NV-Na*Ash Meadows Clinoptilolite that includes hydrous sodium aluminosilicate from St. Cloud Mining Company (Winston, N. Mex.). Table 1 shows typical properties for this zeolite.

TABLE 1

| | |
|---|---|
| Form | Granules & Powders |
| Color | Tan - Green |
| Pore Diameter | 4.0 Angstroms |
| Pore Volume | 15% |
| Specific Surface Area | 40 m²/g |
| Bulk | 45-80 lbs/ft³ |
| | 760-1,283 kg/m³ |
| Solid Density | 100 lbs/ft³ |
| | 1,603 kg/m³ |
| Alkali Stability | pH of 7-10 |
| Acid Stability | pH of 3-7 |
| Thermal Stability | 1,202° F. 650° C. |

A typical chemical analysis for the zeolite can include the component percentages shown in Table 2.

TABLE 2

| $SiO_2$ | $Al_2O_3$ | $Fe_2O_3$ | CaO | MgO | $Na_2O$ | $K_2O$ | MnO | $TiO_2$ |
|---|---|---|---|---|---|---|---|---|
| 69.1 | 11.9 | 0.7 | 0.8 | 0.4 | 3.5 | 3.8 | 0.02 | 0.1 |

The zeolite can exhibit ion exchange with the following cations: $Rb^+$, $Na^+$, $Ba^{+2}$, $Mg^{+2}$, $Li^+$, $Ag^+$, $Sr^{+2}$, $Fe^{+3}$, $K^+$, $Cd^{+2}$, $Cu^{+2}$, $Co^{+3}$, $Cs^+$, $Pb^{+2}$, $Ca^{+2}$, $Al^{+3}$, $NH_4^+$, $Zn^{+2}$, $Hg^{+2}$, and $Cr^{+3}$.

Water-soluble hydrolyzed clinoptilolite fragments can be produced as follows. A hydrolysis reaction can be used to produce the water-soluble hydrolyzed clinoptilolite fragments, where the hydrolysis reaction progress can be monitored over time; e.g., the hydrolysis reaction can proceed over several hours to several days. In certain embodiments, the hydrolysis reaction can be performed over the course of a day. The hydrolysis product (i.e., water-soluble hydrolyzed clinoptilolite fragments) can be recovered, for example, by siphoning and filtering the product.

The hydrolysis reaction can include the following aspects. A reaction mixture can be prepared including clinoptilolite, an acid (e.g., phosphoric acid), and water. The reaction mixture can be assembled by heating the water and adding the clinoptilolite while agitating the reaction mixture in some fashion, for example, by stirring the heated water while dispensing the clinoptilolite at a rate that minimizes clumping in order to form a relatively uniform slurry. The phosphoric acid can be added to the clinoptilolite-water mixture. Addition of the phosphoric acid can be at a rate that maintains a desired temperature profile for the reaction mixture, where agitation or stirring can maintain the reaction mixture as a slurry during the phosphoric acid addition. Heating can be continued as necessary for completion of the hydrolysis reaction. Once completed, the reaction mixture can be allowed to cool.

Completion of the hydrolysis reaction can be monitored as follows. At various time intervals, such as every hour, half-hour, or quarter-hour, stirring and heating of the reaction mixture can be stopped. Morphology of the mixture surface can be observed. Heating and stirring of the reaction mixture can be continued if the hydrolysis reaction is not yet complete. The hydrolysis reaction and monitoring thereof can be continued.

Siphoning and filtration of the hydrolysis reaction product can include the following aspects. The hydrolysis reaction product can be cooled to room temperature and the reaction mixture can be allowed to settle. Settling can result in two layers or portions, including a substantially liquid layer or portion and a substantially solid layer or portion, where the liquid layer includes the hydrolysis reaction product. The liquid layer can be separated from the solid layer by siphoning and/or decanting. The liquid layer can be further filtered to obtain a substantially transparent liquid that can have a light yellowish tint. The liquid layer can be stored thereafter, where storage can include refrigeration of the liquid layer.

The liquid layer including the hydrolysis reaction product can be characterized as follows. The liquid layer can have an acidic pH, for example, a pH that can range from 4.5 to 5.5, including a range of 4.7 to 4.9. The liquid layer can have a solid portion, for example, a solid portion of about 15-21 mg/ml, including about 17-19 mg/ml. Determination of solids can be performed by taking a certain volume of the liquid layer including the hydrolysis reaction product (e.g., 30-50 ml) and allowing the liquid portion to evaporate. For example, the liquid layer volume can be placed on an evaporating plate and left in a warm chamber at 60° C. for 24 hours. The solid portion can be weighed once the liquid is evaporated.

Water-soluble hydrolyzed clinoptilolite fragments in the hydrolysis product can be characterized as follows. Liquid chromatography with mass spectrometry (LC-MS) can be performed to determine the transformation of non-water-soluble zeolite clinoptilolite to water-soluble hydrolyzed clinoptilolite fragments. Suitable equipment for performing LC-MS include an Agilent 1200 HPLC, Agilent 6210 TOF Mass Spectrometer with Electrospray Ionization. The hydrolysis product including the water-soluble hydrolyzed clinoptilolite fragments can be diluted into a mobile phase for analysis by direct injection mass spectrometry. The mobile phase can include 50/50 acetonitrile/water with 0.1% formic acid. The sample can be injected into the mobile phase stream, which can be electrosprayed into the TOF mass spectrometer. LC-MS can confirm that the result of the zeolite clinoptilolite hydrolysis as described herein is an aqueous solution of hydrolyzed zeolite clinoptilolite derived fragments.

FIGS. 1-6 each provide an example of a mass spectrum obtained for six different preparations of water-soluble hydrolyzed clinoptilolite fragments. As can be seen, mass spectrometric analysis of the water-soluble hydrolyzed clinoptilolite fragments can yield a range of molecular weights ranging from 218 to 620 Daltons. The exact mass for each of the observed peaks and the difference between adjacent peaks can be used to determine the presence of sodium ions. At least one sodium ion can be associated with each of the various molecular weight species of water-soluble hydrolyzed clinoptilolite fragments. Repeating units of 98 Daltons and 120 Daltons can be observed. The water-soluble hydrolyzed clinoptilolite fragments have substantially lower molecular weights than the starting zeolite material, where these lower molecular weights can contribute to the water-soluble nature of the hydrolyzed clinoptilolite fragments and can contribute to improved absorption and uptake of the water-soluble hydrolyzed clinoptilolite fragments in the body.

Water-soluble hydrolyzed clinoptilolite fragments can be provided alone and in various compositions and formulations, including various supplement combinations and nutraceutical products. As described herein, the precursor material used to produce the water-soluble hydrolyzed clinoptilolite fragments is the natural zeolite clinoptilolite. Nutraceutical products including food additives can be subject to premarket review and approval by the U.S. Food & Drug Administration (FDA), where under FDA 21 CFR they can be granted GRAS (Generally Regarded As Safe) status. The zeolite clinoptilolite (sodium aluminosilicate) has an FDA GRAS Status as of April 2014 (FDA 21 CFR §182.2727 and food additive E-number: E-554). The starting zeolite material, along with several of the additional components described herein, can be found on the Toxic Substances Control Act List as GRAS materials.

Water-soluble hydrolyzed clinoptilolite fragments can be diluted to desired amounts or percentages by weight. For example, the hydrolysis product obtained using the methods described herein can have a solid portion of about 15-21 mg/mL, corresponding to 1.5-2.1% by weight water-soluble hydrolyzed clinoptilolite fragments. Dilution can be with sterile, distilled, and deionized water. Solutions of the water-soluble hydrolyzed clinoptilolite fragments and water used to dilute the water-soluble hydrolyzed clinoptilolite fragments can also include various stabilizers and/or preservatives. For example, sodium benzoate and/or potassium sorbate can be used. The water-soluble hydrolyzed clinoptilolite fragments can be diluted with water and optional stabilizers and/or preservative(s) to produce solutions have certain pH values and solid portions. For example, diluted water-soluble hydrolyzed clinoptilolite fragment solutions can have a pH of 4.0±1 and a solid portion of 0.35-9.00 mg/ml (i.e. 0.35%-0.9% by weight).

The special water-soluble nature of the water-soluble hydrolyzed clinoptilolite fragments provides certain benefits and advantages when administering the water-soluble hydrolyzed clinoptilolite fragments. For example, oral administration of the water-soluble hydrolyzed clinoptilolite fragments can result in GI absorption of at least a portion of the water-soluble hydrolyzed clinoptilolite fragments. The absorbed water-soluble hydrolyzed clinoptilolite fragments can pass into the blood and be transported to various parts of the body to provide various benefits and advantages. Non-limiting examples of such benefits include: binding heavy metals/environmental toxins for detoxification; absorption at the cellular level; passing into adipose tissue, where heavy metals can accumulate or can be stored within adipose tissue; reduction of reactive oxygen species and inflammation related thereto; providing an increase in energy; and providing an increase in one or more of focus, concentration, and memory.

The water-soluble hydrolyzed clinoptilolite fragments can be used alone and can be used as a component in various compositions that include one or more various dietary supplements, such as one or more various vitamins and/or one or more various nutraceuticals. Non-limiting examples of dietary supplements further include vitamins, minerals, fiber, fatty acids, amino acids, herbs, herbal extracts, and combinations thereof. The dietary supplement can include a water-soluble vitamin, such as one or more of vitamin $B_1$, vitamin $B_2$, vitamin $B_3$, vitamin $B_5$, vitamin $B_6$, vitamin $B_7$, vitamin $B_9$, vitamin $B_{12}$, and vitamin C. In certain embodiments, such dietary supplements are not intended to diagnose, treat, cure, or prevent any disease. The water-soluble hydrolyzed clinoptilolite fragments can also be used to chelate or scavenge various metals, including toxic metals, where the water-soluble hydrolyzed clinoptilolite fragments can facilitate detoxification.

In certain embodiments, the water-soluble hydrolyzed clinoptilolite fragments can be combined with vitamin C (i.e., ascorbic acid), including various salts, derivatives, and esters thereof. Vitamin C receptors exist in the GI tract and in endothelial cells of various barrier tissues in the human body. Examples include the GLUT1 receptor for uptake of vitamin C as well as glucose. Uptake can therefore occur in the GI tract and across blood vessels. For example, the number of vitamin C receptors can be significantly increased in endothelial cells that are part of the blood-brain barrier. As shown by LC-MS of the water-soluble hydrolyzed clinoptilolite fragments, at least one sodium ion is associated with each of the various molecular weight species of the hydrolyzed clinoptilolite fragments. Thus, the combination of vitamin C with water-soluble hydrolyzed clinoptilolite fragments can provide [hydrolyzed clinoptilolite fragment]-[sodium]-[ascorbic acid] salt. A composition including water-soluble hydrolyzed clinoptilolite fragments and vitamin C can therefore provide a complex between individual water-soluble hydrolyzed clinoptilolite fragments and vitamin C molecule, where an ionic bond can be formed between the sodium ion associated with a water-soluble hydrolyzed clinoptilolite fragment and vitamin C. In this way, the ionically bonded vitamin C molecule can serve as a "targeting device" for cells displaying vitamin C receptors. Such cells can bind the vitamin C molecule complexed with the water-soluble hydrolyzed clinoptilolite fragment and carry the water-soluble hydrolyzed clinoptilolite fragment along during uptake of the vitamin C molecule. One embodiment includes a solution of water-soluble hydrolyzed clinoptilolite fragments combined with vitamin C having the following characteristics: pH of 3.0-4.5; water-soluble hydrolyzed clinoptilolite fragments at 0.35-0.90 mg/mL; vitamin C at 3.5-6.0 mg/mL.

Benefits and advantages of water-soluble hydrolyzed clinoptilolite fragments in combination with vitamin C include the following non-limiting examples: detoxification of heavy metals/environmental toxins; increased absorption at the cellular level; passing into adipose tissue, where heavy metals can accumulate or can be stored within adipose tissue; reducing heavy metals related to inflammation; reducing reactive oxygen species related to inflammation; penetration of the blood-brain barrier, reducing heavy metals related inflammation in the central nervous system (CNS); reducing reactive oxygen species related inflammation in the CNS; providing an increase in energy; and providing an increase in one or more of focus, concentration, and memory.

In certain embodiments, the water-soluble hydrolyzed clinoptilolite fragments can be combined with vitamin C and other components, including one or more sleep aids. Examples of sleep aids include L-tryptophan and Alphawave® Calming Blend (commercially available from Ethical Naturals Inc., where Alphawave® Calming Blend includes purified L-theanine with herbal extracts of chamomile, lemon balm, passion flower, hops, and valerian). Formulations including one or more sleep aids can be used to improve the initiation and maintenance of sleep. The initiation and maintenance of sleep can be related with the production, release, and blood concentration levels of melatonin according to the following pathway:

In the brain, serotonin biosynthesis can depend on the quantity of tryptophan, which crosses the blood-brain barrier. L-theanine (an ingredient of Alphawave® Calming Blend) is an amino acid found in green tea leaves and can function as a natural relaxant. Formulation embodiments can include: water-soluble hydrolyzed clinoptilolite fragments at 0.35-4.5 mg/ml; vitamin-C at 3.5-6.0 mg/ml; L-tryptophan at 1.0-4.0 mg/ml; and Alphawave® Calming Blend at 20-40 mg/ml. Benefits and advantages include the following non-limiting examples: absorption at the cellular level; penetration of the blood-brain barrier; supports smooth initiation and maintenance of sleep; supports relaxation without drowsiness; reduces nervous tension; and sustains a sense of calm with focused energy, without forced spikes and crashes.

A composition including the water-soluble hydrolyzed clinoptilolite fragments can be formulated in various ways, typically for oral administration. Examples include forming the composition into one or more various aqueous solutions, liquid capsules, providing the composition in a liquid or slurry form, and providing the composition as a gel or syrup. The water-soluble hydrolyzed clinoptilolite fragments can also be dried (e.g., lyophilized) or partially dried and provided in a solid or partially solid form, such as a powder or paste. Composition components can be entirely admixed together into a single portion, each provided as a separate portion, or various components can be admixed where the whole composition is provided by more than one portion but where a total number of portions is less than the number of components. Other dosage forms suitable for oral administration can be used. In some embodiments, the water-soluble hydrolyzed clinoptilolite fragments can be formulated for other routes of administration, such as sublingual, rectal, topical, intranasal, inhalation, and ophthalmic routes.

Other components can be included in the composition, such as various excipients, including one or more antiadherents (e.g., magnesium stearate), binders (e.g., saccharides, gelatin, polymers), coatings (e.g., hydroxypropyl methylcellulose, enterics such as waxes, plastics, fibers etc.), disintegrants (e.g., polyvinylpyrrolidone, carboxymethyl cellulose, modified starches), flavors, colors, lubricants (e.g., talc, silica, fats), glidants (e.g., fumed silica, talc, magnesium carbonate), sorbents, preservatives (e.g., antioxidants such as vitamins A, E, and C; sodium benzoate; potassium sorbate), and sweeteners.

EXAMPLES

The following protocol was used to produce water-soluble hydrolyzed clinoptilolite fragments by hydrolyzing zeolite.

A hydrolysis reaction was assembled as follows, where the reaction mixture included 1 molar zeolite clinoptilolite and 0.16 molar phosphoric acid in UV Treated R/O water.
1. A stainless steel pot was placed over a heating plate.
2. Filtered and UV Treated Reverse Osmosis water was added in the stainless steel pot and stirring was initiated.
3. Under constant stirring, 1 M of clinoptilolite was transferred slowly to the stainless steel pot.
4. The mixture of clinoptilolite-water was heated to 170-175° F. (77-79° C.)
5. 0.16 M of phosphoric acid (85%) was added to the clinoptilolite-water mixture under constant stirring. This time-point of the hydrolysis reaction was time-point zero.
6. Under constant stirring the mixture was further heated to 170-175° F. (77-79° C.) as needed for the completion of the hydrolysis reaction.
7. Once the hydrolysis reaction was completed, stirring and heating stopped. The stainless steel pot with the mixture was immediately removed from the heating plate surface and left to cool at room temperature for 24 hours.

At various time intervals after time-point zero, such as every hour, half-hour, or quarter-hour, stirring and heating of the reaction mixture can be stopped. Morphology of the mixture surface can be observed. Heating and stirring of the reaction mixture can be continued if the hydrolysis reaction is not yet complete. The hydrolysis reaction and monitoring thereof can be continued.

Siphoning and filtering of the hydrolysis reaction product included the following aspects.
1. The reaction mixture was cooled at room temperature.
2. Two distinct layers were formed in the pot as the result of the hydrolysis reaction—a liquid layer and a solid layer.
3. Siphoning of the liquid layer was vacuum initiated and gravity assisted.
4. Filtration of the liquid product was performed as needed to collect a transparent liquid with light yellowish tint.
5. The liquid product was placed in a refrigerator.

Quantitative characteristics of the hydrolysis reaction product in the liquid layer included a pH of 4.7-4.9 and a solids content of 15-21 mg/ml. The amount of water-soluble hydrolyzed clinoptilolite fragments in the liquid layer, or the solids content, was determined by placing a certain volume of the hydrolysis reaction (e.g., 30-50 ml) on an evaporating plate and allowing to dry in a warm chamber at 60° C. for 24 hours. The amount of residual solids was measured once the liquid placed in the evaporating plate was fully evaporated.

Analytical chemistry testing for water-soluble hydrolyzed clinoptilolite fragments included the following. Liquid chromatography with mass spectrometry (LC-MS) was performed to test the successful transformation of the non-water-soluble zeolite clinoptilolite to water-soluble clinoptilolite fragments. LC-MS confirmed that the result of the zeolite clinoptilolite hydrolysis as described above resulted in an aqueous solution of water-soluble zeolite clinoptilolite derived fragments. LC-MS analysis was performed using an Agilent 1200 HPLC, an Agilent 6210 TOF Mass Spectrometer with Electrospray Ionization. The hydrolysis product was diluted in the mobile phase for analysis by direct injection mass spectrometry. The mobile phase consisted of 50/50 acetonitrile/water with 0.1% formic acid. The sample was injected into the mobile phase stream, which was electrosprayed into the TOF mass spectrometer.

Six different preparations of water-soluble hydrolyzed clinoptilolite fragments were analyzed.

Figure 1:
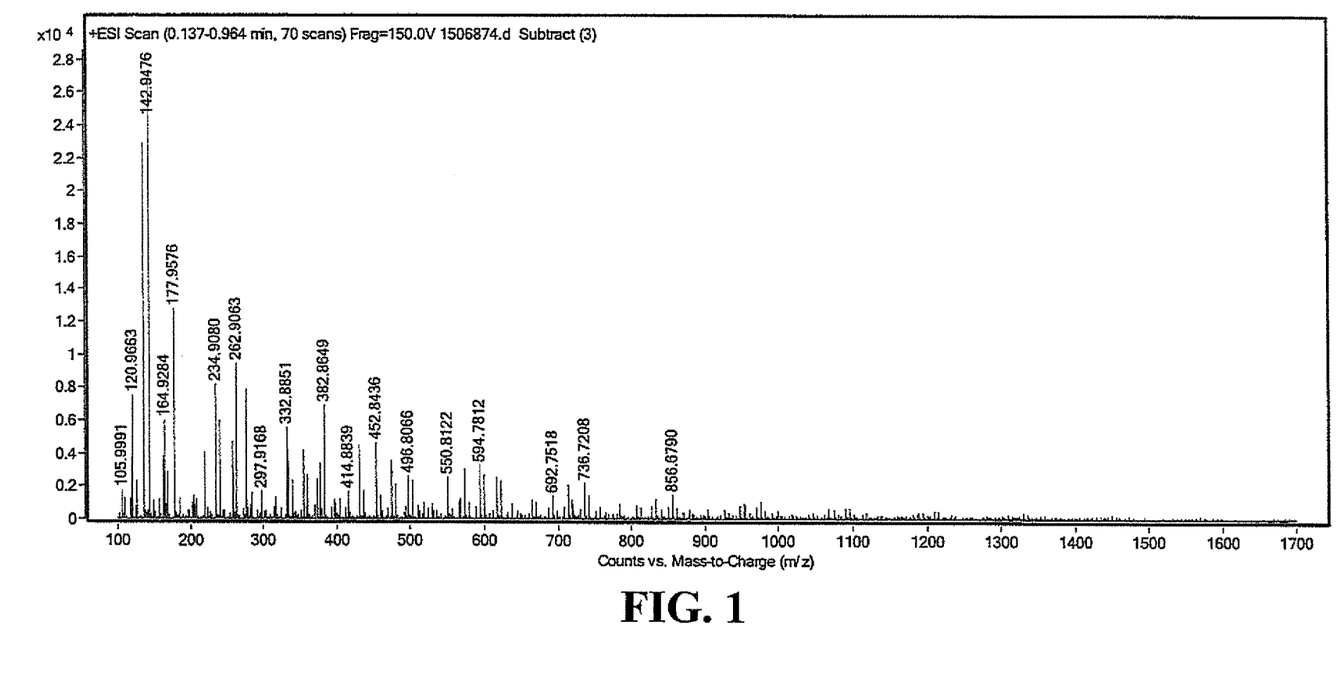
FIG. 1 depicts a spectrogram obtained from liquid chromatography-mass spectrometry (LC-MS) analysis of water-soluble hydrolyzed clinoptilolite fragments having a range of molecular weights between 218-620 Daltons produced according to the present technology.

FIG. 1 shows a spectrogram for the first water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 2:
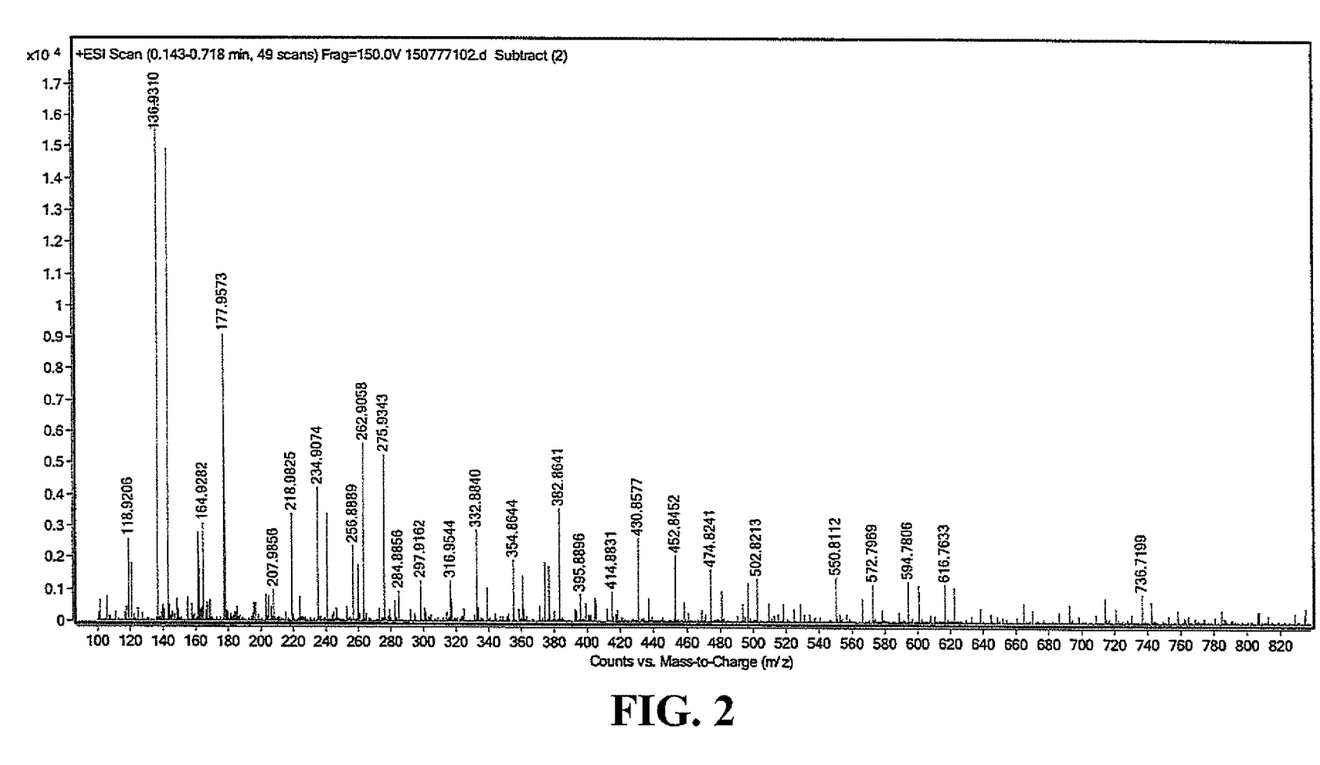
FIG. 2 depicts another spectrogram obtained from LC-MS analysis of another preparation of water-soluble hydrolyzed clinoptilolite fragments having a range of molecular weights between 218-620 Daltons produced according to the present technology.

FIG. 2 shows a spectrogram for the second water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 3:
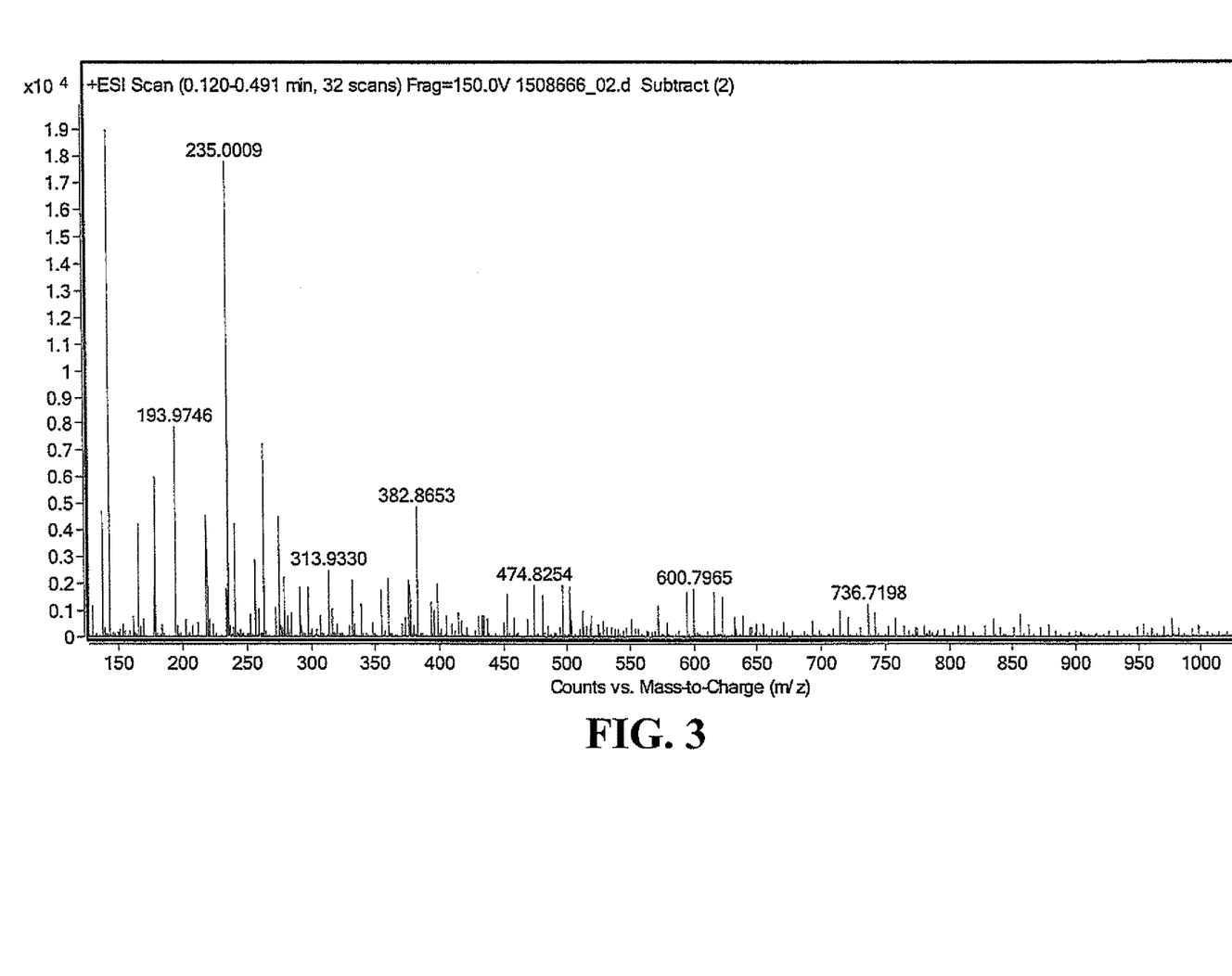
FIG. 3 depicts yet another spectrogram obtained from LC-MS analysis of yet another preparation of water-soluble hydrolyzed clinoptilolite fragments having a range of molecular weights between 218-620 Daltons produced according to the present technology.

FIG. 3 shows a spectrogram for the third water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 4:
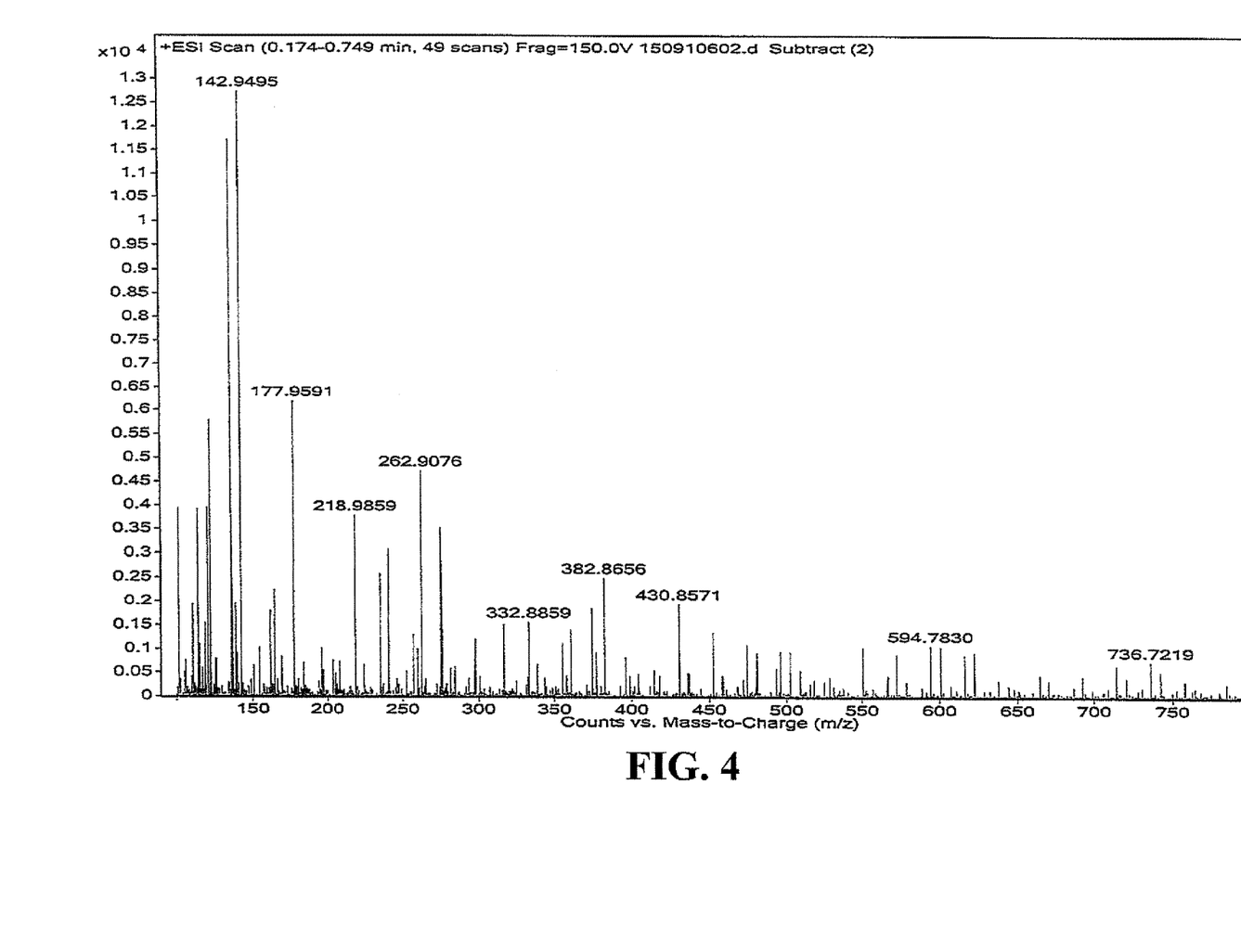
FIG. 4 depicts yet another spectrogram obtained from LC-MS analysis of yet another preparation of water-soluble hydrolyzed clinoptilolite fragments having a range of molecular weights between 218-620 Daltons produced according to the present technology.

FIG. 4 shows a spectrogram for the fourth water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 5:
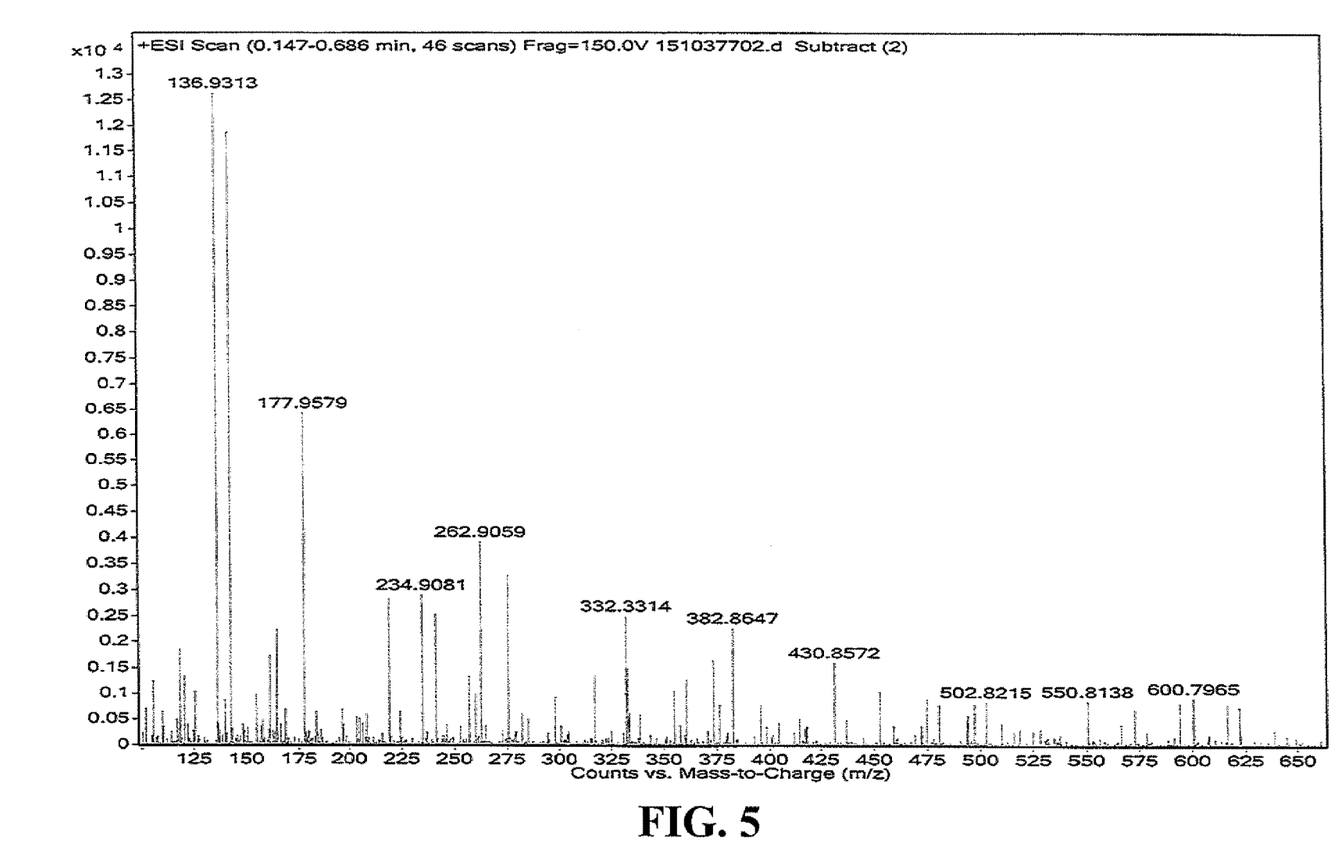
FIG. 5 depicts yet another spectrogram obtained from LC-MS analysis of yet another preparation of water-soluble hydrolyzed clinoptilolite fragments having a range of molecular weights between 218-620 Daltons produced according to the present technology.

FIG. 5 shows a spectrogram for the fifth water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Figure 6:
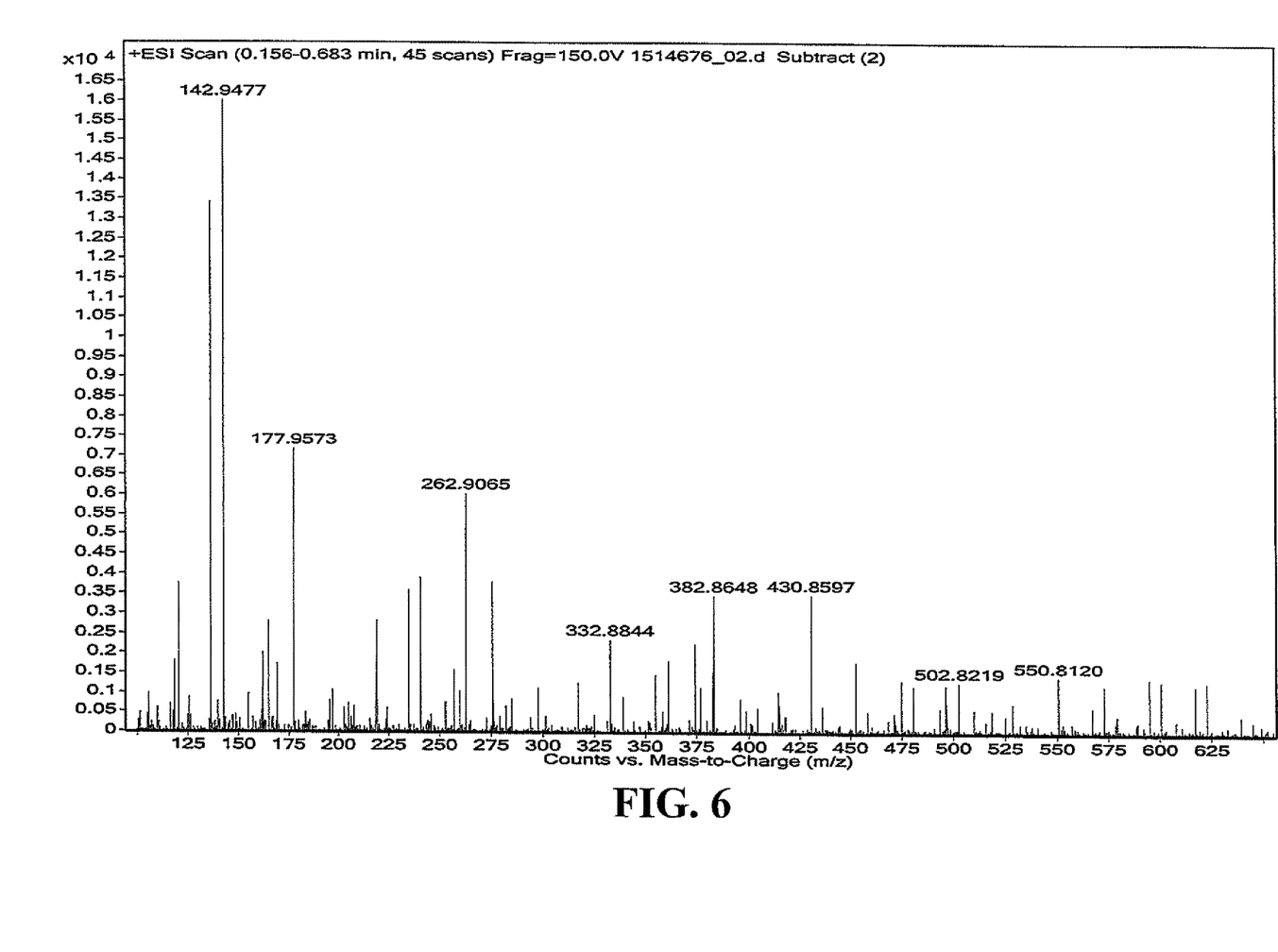
FIG. 6 depicts yet another spectrogram obtained from LC-MS analysis of yet another preparation of water-soluble hydrolyzed clinoptilolite fragments having a range of molecular weights between 218-620 Daltons produced according to the present technology.

FIG. 6 shows a spectrogram for the sixth water-soluble hydrolyzed clinoptilolite fragment preparation including species having a range of molecular weights between 218-620 Daltons, where the exact mass for each of the observed peaks and the difference between adjacent peaks was used to determine the presence of sodium ions, indicating at least one sodium ion associated with each of the various molecular weight species. There was evidence for sodium-proton interchange based on (+/−22 Da) spacing. Repeating units of 98 and 120 Daltons were detected.

Two preparations of water-soluble hydrolyzed clinoptilolite fragments (Preparation #1 and Preparation #2) were analyzed by X-ray diffraction (XRD). A Philips-Norelco Model 3000 XRD unit containing a step scanning goniometer was used for XRD analysis. For each Preparation a sample of a water solution of hydrolyzed clinoptilolite fragments was initially dried to constant weight at ambient temperature and low humidity, then pulverized with a ceramic mortar and pestle to less than 200 mesh. For XRD analysis, this pulverized sample of hydrolyzed clinoptilolite fragments was back loaded as a randomly oriented powder and compressed into a sample holder at 5 psi. The XRD ranges are from 3° to 70° 2theta for powder samples and 2° to 18° 2theta for oriented coatings.

The starting zeolite clinoptilolite was analyzed by X-ray diffraction (XRD). A Philips-Norelco Model 3000 XRD unit containing a step scanning goniometer was used for XRD analysis. A sample of zeolite clinoptilolite powder was initially dried to constant weight at ambient temperature and low humidity, and then pulverized with a ceramic mortar and pestle to less than 200 mesh. For XRD analysis, this pulverized sample of starting zeolite clinoptilolite was back loaded as a randomly oriented powder and compressed into a sample holder at 5 psi. The XRD ranges are from 3° to 70°2theta for powder samples and 2° to 18° 2theta for oriented coatings. For smectite clay detection, a portion of this clinoptilolite sample was slurried in distilled water, followed by coating a slurry onto a glass microscope slide. As this slurry dries, any dispersed smectite clay platelets orient parallel to the glass slide, enhancing its (0,0,X) layer diffraction peaks. After XRD evaluation of this oriented coating from 20 to 18°2theta, it was exposed to ethylene glycol vapor for a minimum of 4 hours at 50° C. then reevaluated by XRD. With exposure to ethylene glycol, any expandable smectite (0,0,1) layer diffraction peak expands to 17 Angstroms, confirming that smectite is not present in a sample. Quartz concentrations are reported to the nearest 0.1%. The XRD results for the starting zeolite clinoptilolite are reported in Table 3 below.

TABLE 3

| | % clinoptilolite | % quartz | % smectite |
|---|---|---|---|
| starting zeolite | 99% | 1.0% | <0.5% |

Figure 7:
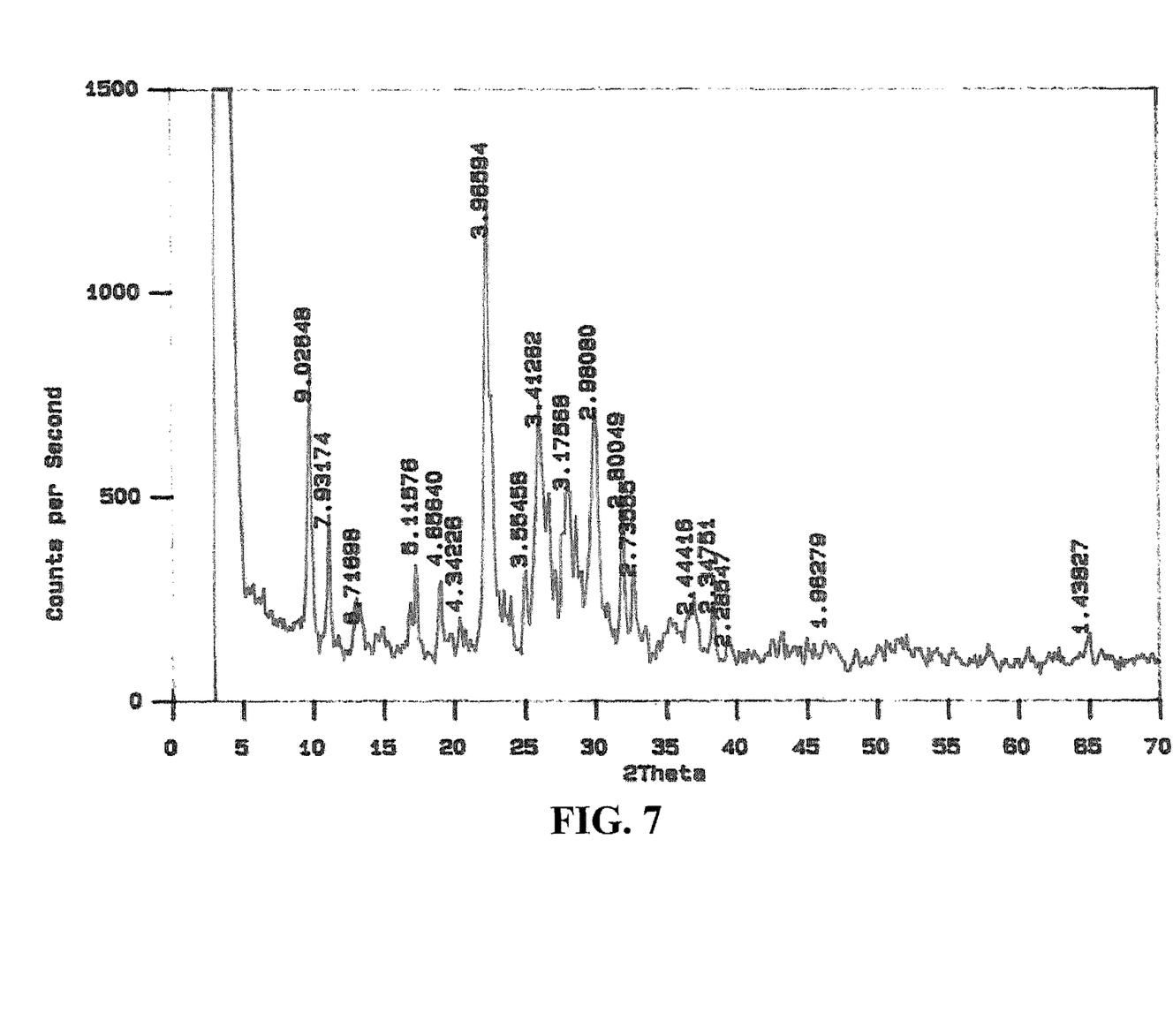
FIG. 7 depicts an X-ray diffraction (XRD) pattern for a starting zeolite clinoptilolite material.

The XRD pattern for the starting zeolite material is shown in FIG. 7.

Figure 8:
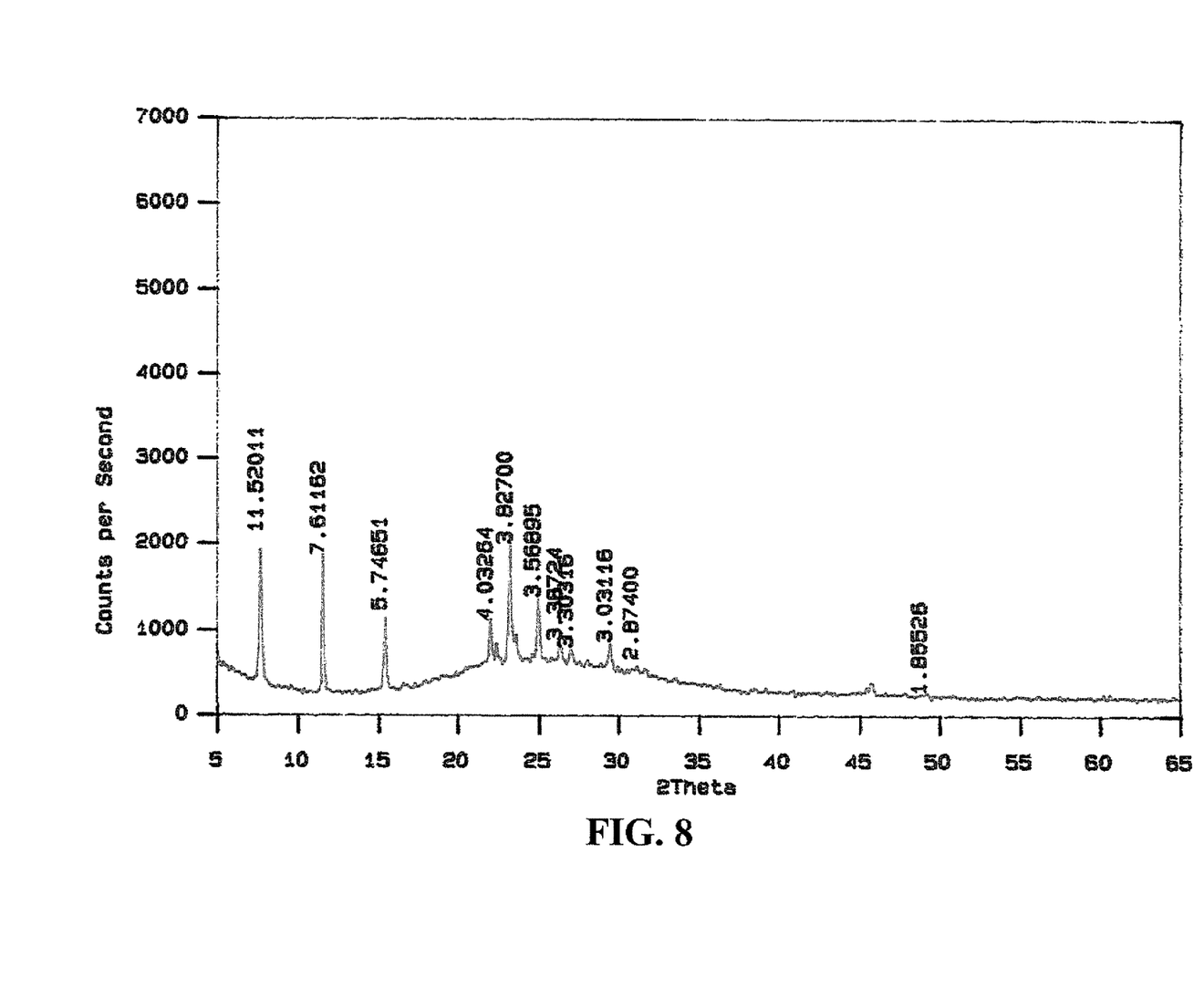
FIG. 8 depicts the XRD pattern for a preparation of water-soluble hydrolyzed clinoptilolite fragments (Preparation #1).

The XRD pattern for the first preparation of water-soluble hydrolyzed clinoptilolite fragments (Preparation #1) is shown in FIG. 8.

Figure 9:
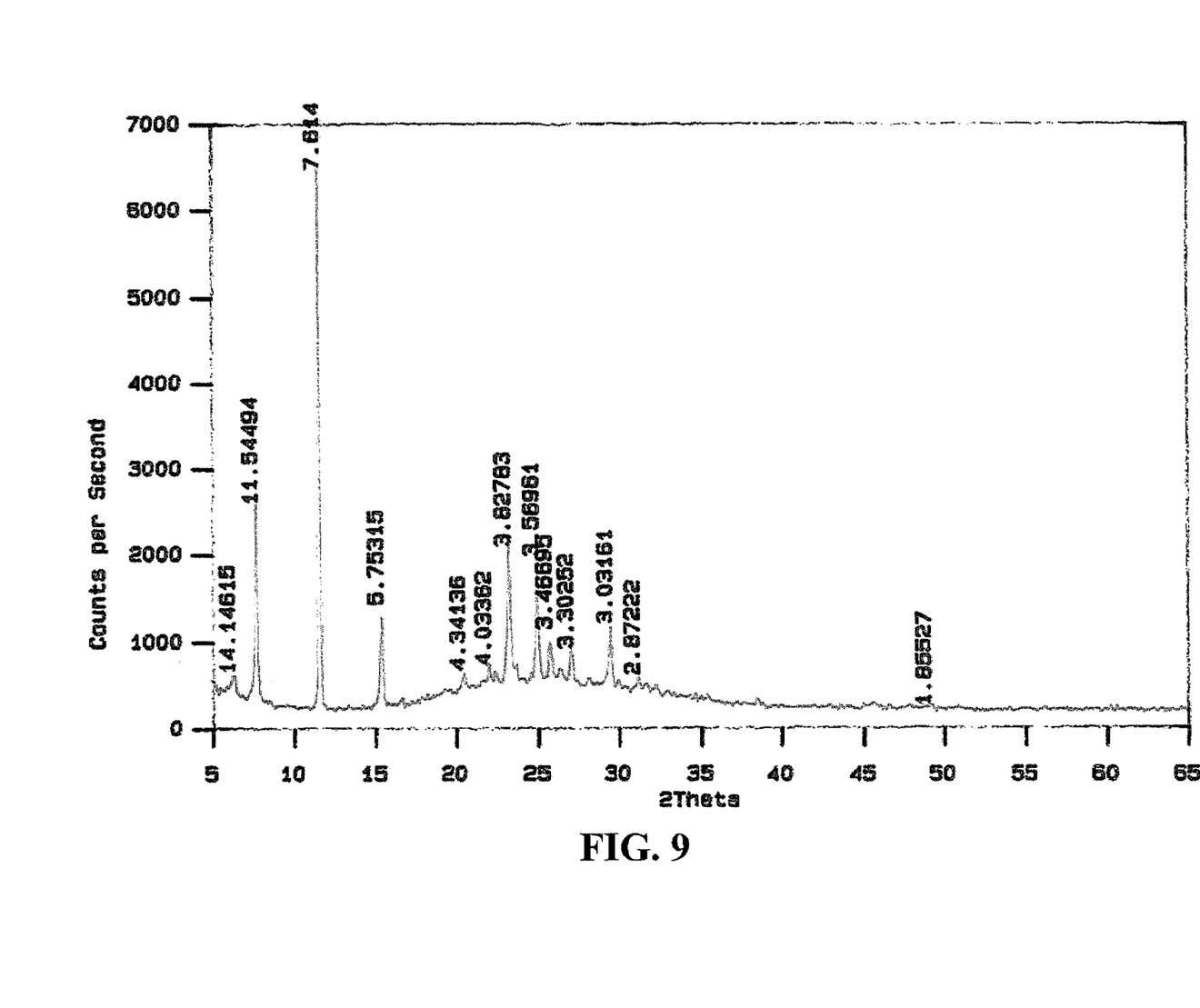
FIG. 9 depicts the XRD pattern for another preparation of water-soluble hydrolyzed clinoptilolite fragments (Preparation #2).

The XRD pattern for the second preparation of water-soluble hydrolyzed clinoptilolite fragments (Preparation #2) is shown in FIG. 9.

Table 4 shown below lists the XRD peak locations (in Angstroms) for the two different preparations of water-soluble hydrolyzed clinoptilolite fragments (Preparation #1 and Preparation #2) and the starting zeolite clinoptilolite (sodium aluminosilicate from Ash Meadows, Nev. obtained from St. Cloud Mining Company (Winston, N. Mex.)).

TABLE 4

| Preparation #1 | Preparation #2 | Starting Zeolite |
|---|---|---|
| — | 14.14 | — |
| 11.52 | 11.54 | — |
| — | — | 9.03 |
| — | — | 7.93 |
| 7.61 | 7.61 | — |
| — | — | 6.72 |
| 5.75 | 5.75 | — |
| — | — | 5.12 |
| — | 4.34 | — |
| 4.03 | 4.03 | 3.965 |
| 3.827 | 3.827 | — |
| 3.569 | 3.569 | 3.555 |
| 3.387 | 3.386 | 3.412 |
| 3.303 | 3.302 | — |
| — | — | 3.176 |
| — | — | 2.981 |
| 2.874 | 2.874 | — |
| — | — | 2.801 |
| — | — | 2.347 |
| — | — | 2.285 |
| 1.855 | 1.855 | — |
| — | — | 1.438 |

As can be seen in Table 4 and FIGS. 8 and 9, the results of XRD analysis of the two preparations of water-soluble hydrolyzed clinoptilolite fragments (Preparations #1 and #2) were similar. It is noted that FIGS. 8 and 9 record a broad baseline bulge between 18° and 35°2theta that appears to be due to the detection of amorphous (noncrystalline) material fragments. It is apparent that the hydrolysis reaction has transformed the starting zeolite clinoptilolite material in producing the water-soluble hydrolyzed clinoptilolite fragments.

Based upon the LC-MS data, the water-soluble hydrolyzed clinoptilolite fragments have molecular weights ranging between 218-620 Daltons. The molecular weight of a unit cell of the starting zeolite clinoptilolite material is approximately 474 g/mol, where it is noted that individual unit cells can vary in chemical composition, especially with associated exchange cations. Therefore, the charged particles (i.e., the water-soluble hydrolyzed clinoptilolite fragments) separated by liquid chromatography, which were subsequently characterized by mass spectroscopy, appear to contain from 0.46 to 1.31 clinoptilolite unit cells. Without wishing to be bound by theory, it is believed that the water-soluble hydrolyzed clinoptilolite fragments include fragments of unit cells derived from the starting zeolite clinoptilolite, where the hydrolysis reaction has served to fragment the repeating unit cell structure of the zeolite clinoptilolite at various labile positions to give clinoptilolite fragments including complete unit cells, incomplete unit cells, and complete unit cells that remain coupled to remnants of formerly adjacent unit cells.

The XRD pattern for the water-soluble hydrolyzed clinoptilolite fragments can provide a fingerprint and a way to identify the special hydrolysis products created using the present technology. For example, XRD peaks unique to the water-soluble hydrolyzed clinoptilolite fragments that are absent from the starting zeolite can provide a defining attribute of the water-soluble hydrolyzed clinoptilolite fragments. Examples of such peak values in angstroms are listed in Table 4 as 11.54, 7.61, 5.75, 3.827, 3.303, 2.874, and 1.855. Accordingly, one or more of these peaks can be used to define or identify the water-soluble hydrolyzed clinoptilolite fragments produced by the hydrolysis reaction described herein and distinguish the hydrolyzed clinoptilolite fragments from the starting zeolite clinoptilolite material. The water-soluble hydrolyzed clinoptilolite fragments can therefore be distinguished by one or more characteristic peaks in the X-ray diffraction pattern at 11.5+/−0.1 angstroms, 7.6+/−0.1 angstroms, 5.8+/−0.1 angstroms, 3.8+/−0.1 angstroms, 3.3+/−0.1 angstroms, 2.9+/−0.1 angstroms, and 1.9+/−0.1 angstroms.

Alternatively or in addition to, the water-soluble hydrolyzed clinoptilolite fragments can be distinguished by one or more characteristic peaks in the powder X-ray diffraction pattern at the unique values of 2theta as shown in FIGS. 7 and 8 versus the starting zeolite material in FIG. 6. For example, one or more unique 2theta values (in degrees) can provide a fingerprint and a way to identify the special hydrolysis products created using the present technology. The respective 2theta values for the peaks labeled 11.54, 7.61, 5.75, 3.827, 3.303, 2.874, and 1.855 are 7.5°, 11°, 15°, 23°, 26°, 31°, and 49°. The 2theta values can also be assigned a standard deviation or standard error of +/−0.1°.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A composition comprising an aqueous solution of water-soluble hydrolyzed clinoptilolite fragments and vitamin C,
   wherein the composition has a pH of 3.0 - 4.5, and the water-soluble hydrolyzed clinoptilolite fragments are present at about 0.35 - 0.9 mg/ml, and the vitamin C is present at about 3.5 - 6.0 mg/ml, and
   wherein the water-soluble hydrolyzed clinoptilolite fragments are formed by hydrolyzing zeolite clinoptilolite with acid, and separating the hydrolyzed zeolite clinoptilolite into a liquid portion and a solid portion, the liquid portion including the water-soluble hydrolyzed clinoptilolite fragments.

2. The composition of claim 1, wherein the water-soluble hydrolyzed clinoptilolite fragments includes a plurality of fragments having molecular weights ranging from about 218 Daltons to about 620 Daltons.

3. The composition of claim 1, wherein the water-soluble hydrolyzed clinoptilolite fragments are derived from zeolite comprising about 99% clinoptilolite, the clinoptilolite comprising sodium aluminosilicate.

4. The composition of claim 1, wherein about 1 sodium ion is associated with each fragment.

5. The composition of claim 1, wherein the water-soluble hydrolyzed clinoptilolite fragments include repeating units of about 98 Daltons and about 120 Daltons.

6. The composition of claim 1, wherein the water-soluble hydrolyzed clinoptilolite fragments includes a plurality of fragments having molecular weights ranging from about 218 Daltons to about 620 Daltons, at least one sodium ion is associated with each fragment, and the fragments include repeating units of about 98 Daltons and about 120 Daltons.

7. The composition of claim 1, wherein the water-soluble hydrolyzed clinoptilolite fragments include at least one peak in the X-ray diffraction pattern selected from the group consisting of 11.5 +/−0.1 angstroms, 7.6 +/−0.1 angstroms, 5.8 +/−0.1 angstroms, 3.8 +/−0.1 angstroms, 3.3 +/−0.1 angstroms, 2.9 +/−0.1 angstroms, 1.9 +/−0.1 angstroms, and combinations thereof.

8. The composition of claim 1, wherein the water-soluble hydrolyzed clinoptilolite fragments include X-ray diffraction pattern peaks at 11.5 +/−0.1 angstroms, 7.6 +/−0.1 angstroms, 5.8 +/−0.1 angstroms, 3.8 +/−0.1 angstroms, 3.3 +/−0.1 angstroms, 2.9 +/−0.1 angstroms, and 1.9 +/−0.1 angstroms.

9. The composition of claim 1, wherein the water-soluble hydrolyzed clinoptilolite fragments have characteristic peaks in the X-ray diffraction pattern at values of two theta of 7.5°+/−0.1°, 11°+/−0.1°, 15°+/−0.1°, 23°+/−0.1°, 26°+/−0.1°, 31°+/−0.1°, and 49°+/−0.1°.

10. The composition of claim 1, further comprising a dietary supplement.

11. The composition of claim 10, wherein the dietary supplement includes a member selected from the group consisting of a vitamin, mineral, fiber, fatty acid, amino acid, herb, herbal extract, and combinations thereof.

12. The composition of claim 10, wherein the dietary supplement includes a water-soluble vitamin selected from the group consisting vitamin $B_1$, vitamin $B_2$, vitamin $B_3$, vitamin $B_5$, vitamin $B_6$, vitamin $B_7$, vitamin $B_9$, vitamin $B_{12}$, and combinations thereof.

13. The composition of claim 1, wherein the water-soluble hydrolyzed clinoptilolite fragments are complexed with an ion.

14. The composition of claim 13, wherein the ion includes a metal ion.

15. The composition of claim 1, further comprising a sleep aid, wherein the sleep aid includes a member selected from the group consisting of L-tryptophan, L-theanine, chamomile, lemon balm, passion flower, hops, valerian, and combinations thereof.

16. A composition comprising an aqueous solution of water-soluble hydrolyzed clinoptilolite fragments, vitamin C, L-tryptophan, and a sleep aid combination including chamomile, lemon balm, passion flower, hops, and valerian,
   wherein the composition has a pH of 3.0 - 4.5, and the water-soluble hydrolyzed clinoptilolite fragments are present at about 0.35 - 4.5 mg/ml, the vitamin C is present at about 3.5 - 6 mg/ml the L-tryptophan is present at about 1.0 - 4.0 mg/ml and the sleep aid combination is present at about 20 - 40 mg/ml, and
   wherein the water-soluble hydrolyzed clinoptilolite fragments are formed by hydrolyzing zeolite clinoptilolite with acid, and separating the hydrolyzed zeolite clinoptilolite into a liquid portion and a solid portion, the liquid portion including the water-soluble hydrolyzed clinoptilolite fragments.

* * * * *

UNITED STATES PATENT AND TRADEMARK OFFICE
CERTIFICATE OF CORRECTION

PATENT NO. : 9,629,874 B2
APPLICATION NO. : 14/879233
DATED : April 25, 2017
INVENTOR(S) : Tsirikos-Karapanos It is certified that error appears in the above-identified patent and that said Letters Patent is hereby corrected as shown below:

Column 14, Lines 7-19, Claim 1 should read:
A composition comprising an aqueous solution of water-soluble hydrolyzed clinoptilolite fragments and vitamin C, wherein the composition has a pH of 3.0 – 4.5, and the water-soluble hydrolyzed clinoptilolite fragments are present at about 0.35 – 0.9 mg/ml, and the vitamin C is present at about 3.5 – 6.0 mg/ml, and wherein the water-soluble hydrolyzed clinoptilolite fragments are formed by hydrolyzing zeolite clinoptilolite with acid, and separating the hydrolyzed zeolite clinoptilolite into a liquid portion and a solid portion, the liquid portion including the water-soluble hydrolyzed clinoptilolite fragments, at least one of the water-soluble hydrolyzed clinoptilolite fragments comprising alumina.

Column 15, Lines 11-26, Claim 16 should read:
A composition comprising an aqueous solution of water-soluble hydrolyzed clinoptilolite fragments, vitamin C, L-tryptophan, and a sleep aid combination including chamomile, lemon balm, passion flower, hops, and valerian, wherein the composition has a pH of 3.0 – 4.5, and the water-soluble hydrolyzed clinoptilolite fragments are present at about 0.35 – 4.5 mg/ml, the vitamin C is present at about 3.5 – 6 mg/ml, the L-tryptophan is present at about 1.0 – 4.0 mg/ml and the sleep aid combination is present at about 20 – 40 mg/ml, and wherein the water-soluble hydrolyzed clinoptilolite fragments are formed by hydrolyzing zeolite clinoptilolite with acid, and separating the hydrolyzed zeolite clinoptilolite into a liquid portion and a solid portion, the liquid portion including the water-soluble hydrolyzed clinoptilolite fragments, at least one of the water-soluble hydrolyzed clinoptilolite fragments comprising alumina.

Signed and Sealed this
Fifth Day of December, 2017

Joseph Matal
*Performing the Functions and Duties of the
Under Secretary of Commerce for Intellectual Property and
Director of the United States Patent and Trademark Office*